(12) United States Patent
Weiss

(10) Patent No.: US 7,793,379 B2
(45) Date of Patent: Sep. 14, 2010

(54) CONTINUOUS FEED INTER-DENTAL BRUSH ASSEMBLY AND DEVICE

(76) Inventor: Roger E. Weiss, 1742 Naudain St., Philadelphia, PA (US) 19146

( * ) Notice: Subject to any disclaimer, the term of this patent is extended or adjusted under 35 U.S.C. 154(b) by 379 days.

(21) Appl. No.: 12/148,819

(22) Filed: Apr. 23, 2008

(65) Prior Publication Data
US 2008/0202549 A1   Aug. 28, 2008

Related U.S. Application Data

(63) Continuation-in-part of application No. 11/602,006, filed on Nov. 20, 2006, now Pat. No. 7,730,572.

(51) Int. Cl.
*A61C 3/00* (2006.01)

(52) U.S. Cl. ......... 15/167.1; 132/328; 433/141

(58) Field of Classification Search ......... 15/167.1, 15/53.4, 169; 132/321, 328; 433/141; *A61C 3/00*; *A46B 9/04, 5/00*
See application file for complete search history.

(56) References Cited

U.S. PATENT DOCUMENTS

| | | | |
|---|---|---|---|
| 3,886,956 A | 6/1975 | Cash | 132/91 |
| 4,005,721 A | 2/1977 | Yasumoto | 132/91 |
| 4,512,354 A | 4/1985 | Loubier et al. | 132/91 |
| 5,060,681 A | 10/1991 | Westbrook | 132/325 |
| 5,085,236 A | 2/1992 | Odneal et al. | 132/325 |
| 5,176,157 A | 1/1993 | Mazza | 132/322 |
| 5,217,031 A | 6/1993 | Santoro | 132/322 |
| 5,269,331 A | 12/1993 | Tanriverdi | 132/325 |
| 5,495,863 A | 3/1996 | Bergman | 132/326 |
| 5,642,741 A | 7/1997 | Choi | 132/329 |
| 5,657,780 A | 8/1997 | Giacopuzzi | 132/325 |
| 5,718,667 A | 2/1998 | Sugimoto et al. | 601/139 |
| 5,722,440 A | 3/1998 | Urso | 132/323 |
| 5,868,149 A | 2/1999 | Yang | 132/328 |
| 6,079,424 A | 6/2000 | Lillbacka | 132/326 |
| 6,363,949 B1 | 4/2002 | Brown | 132/325 |

(Continued)

FOREIGN PATENT DOCUMENTS

| JP | 08-056749 | | 3/1996 |
|---|---|---|---|
| JP | 08056749 A | * | 3/1996 |
| JP | 2004-313446 | | 11/2004 |

*Primary Examiner*—Monica S Carter
*Assistant Examiner*—Stephanie Newton
(74) *Attorney, Agent, or Firm*—Ernest D. Buff; Ernest D. Buff & Associates LLC

(57) ABSTRACT

An inter-dental brush device has a handle with a cartridge removably housed therein. The cartridge has a plurality of chambers each appointed for housing at least one replaceable inter-dental brush. The cartridge is appointed to be rotated to align and select one of the chambers for feed out of the selected inter-dental brush. A base portion is removably attached to the handle, which includes rotation engagement means adapted to interact with the cartridge for rotational engagement, alignment and selection of the chamber and visa vie the inter-dental brush housed therein. An oral portion is removably attached to the other end of the handle, and includes an aperture for feeding out the selected inter-dental brush. A delivery means in association with the handle and the oral portion is provided and is adapted to feed out the selected inter-dental brush. Used, worn out brush is removed or cut off by an optional slidable cutter provided on the brush device.

18 Claims, 5 Drawing Sheets

U.S. PATENT DOCUMENTS

| | | | |
|---|---|---|---|
| 7,011,099 B2 | 3/2006 | Bergman | 132/325 |
| 2005/0000539 A1 | 1/2005 | Bergman | 132/325 |
| 2005/0144747 A1 | 7/2005 | Juan | 15/167.1 |
| 2005/0247328 A1 | 11/2005 | Shen et al. | 132/325 |
| 2006/0011211 A1 | 1/2006 | Landry | 132/325 |
| 2006/0011212 A1 | 1/2006 | Achepohl et al. | 132/325 |

* cited by examiner

CONTINUOUS FEED INTER-DENTAL BRUSH ASSEMBLY AND DEVICE

CROSS-REFERENCE TO RELATED APPLICATIONS

This application is a continuation-in-part of U.S. patent application Ser. No. 11/602,006, which was filed on Nov. 20, 2006 now U.S. Pat. No. 7,730,572, the disclosure of which is hereby incorporated by reference.

BACKGROUND OF THE INVENTION

1. Field of the Invention

The present invention relates to a brush assembly for improving dental hygiene; and, more particularly, to a device wherein a continuous feed of inter-dental brush is achieved by providing a cartridge having a plurality of chambers each housing at least one inter-dental brush therein and being rotatable to a position of alignment with a channel in communication with a nozzle orifice, for selecting a desired inter-dental brush to be fed out of the nozzle orifice for use, excising the used inter-dental brush and facilitating the selection and production of a fresh inter-dental brush upon demand.

2. Description of the Prior Art

Devices for cleaning teeth and removing plaque that is accumulated between teeth are well known in the art. Most commonly used devices include electrically powered toothbrushes, dental floss and inter-dental tooth cleaning brushes. These inter-dental toothbrushes are more effective when the gaps between teeth are adequate for the insertion of the inter-dental brush, and the gaps between teeth are readily accessible. In these cases, where the gaps between the teeth are large, use of dental floss in removing plaque is generally ineffective since the floss fails to contact the entire root surface of the teeth. Inter-dental brushes have become popular in recent times, since they effectively remove plaque that has accumulated between teeth and around the entire tooth-gum interface, which is not readily removed using dental floss.

Numerous patents disclose dental floss holders having means to feed new floss, collect used floss and adjust tension in the dental floss. Very few patents relate to inter-dental brushes. These patents require discrete brushes attached to metallic wire designed for insertion into a slot carried by the brush handle. In this manner, replacement is effected for discrete inter-dental brushes that have become worn. None of the patents envision the use of a cartridge having a plurality of chambers housing at least one inter-dental brush therein that is rotated to present a selected inter-dental brush for use and/or the replacement of a used inter-dental brush with a fresh inter-dental brush from the chambers, yielding a continuous feed stock.

U.S. Pat. No. 3,886,956 to Cash discloses a dental floss holder. This floss holder has a cavity that holds a spool of dental floss and delivers it to the floss head through a pair of pincers that grip the dental floss. The pincers are opened by application of finger pressure to a button provided on the handle of the floss holder. The '956 patent does not disclose delivery of fresh inter-dental brush; it does not disclose a cartridge having a plurality of chambers housing at least one inter-dental brush therein that is rotated to present a selected inter-dental brush for use.

U.S. Pat. No. 4,005,721 to Yasumoto discloses a dental floss holder. The interior of the dental floss holder has a cavity for retaining the dental floss spool. The dental floss is connected to a bifurcated tip, which may be sideways mounted for accessing front teeth, and a bottom-mounting tip for cleaning back teeth. The '721 patent contains no disclosure regarding a brush assembly having cartridge constructed with a plurality of chambers housing at least one inter-dental brush therein that is rotated to present a selected inter-dental brush for use.

U.S. Pat. No. 4,512,354 to Loubier et al. discloses a dental floss applicator with improved floss severing and anchoring. This dental floss applicator has a capstan controllable by the user for tensioning the floss and for periodically substituting a fresh floss strand segment for a previously used segment. An improved arrangement is provided, whereby floss is severed, and a floss strand end is anchored to the capstan by continuous movement of the strand. Such disclosure of a dental floss applicator handle having means for cutting the floss does not suggest delivery of inter-dental brush from a cartridge with a plurality of chambers therein.

U.S. Pat. No. 5,060,681 to Westbrook et al. discloses a dental flossing device. This device uses a continuous dental floss that is fed from a spool to a dental floss head. Used floss is returned to an adjacent spool and both spools are located in the handle. When the supply of fresh floss on the bobbin is exhausted, the device is discarded. The dental flossing device does not deliver an inter-dental brush.

U.S. Pat. No. 5,085,236 to Odneal et al. discloses a dental floss machine. This dental floss machine attaches to a standard electric toothbrush to provide oscillatory motion of the floss. The floss spool is contained within the handle of the machine and the used floss is collected in a separate spool that is on the same shaft as the dental floss supply spool. This dental floss machine does not deliver an inter-dental brush.

U.S. Pat. No. 5,176,157 to Mazza discloses a device for supporting and operation a dental floss. The dental floss is contained within the handle. A motor drive is provided to drive the dental floss into a flossing fork and the used floss is collected within the handle. The motor, in addition to providing drive for the dental floss, also provides a vibratory motion imparted by an RF coil. This dental floss device does not deliver an inter-dental brush. It does not provide a cartridge having a plurality of chambers housing at least one inter-dental brush therein that is rotated to present a selected inter-dental brush for use.

U.S. Pat. No. 5,217,031 to Santoro discloses a motor-driven apparatus for cleaning spaces between teeth by dental floss. This motor-driven apparatus is operative to clean spaces between teeth with dental floss. A motor drive feeds fresh dental floss, collects used dental floss in the pulley and also provides oscillation to the taut dental floss. This device does not deliver an inter-dental brush. No means are provided for a cartridge having a plurality of chambers housing at least one inter-dental brush therein that is rotated to present a selected inter-dental brush for use.

U.S. Pat. No. 5,269,331 to Tanriverdi discloses an automatic locking and adjustable tension controlled dental flosser. This self-contained dental flosser has an adjustable tension control. An auto-tension locking mechanism allows the flosser to operate and advance the floss continuously in one direction by rotating a spool wherein spool gears extend out of the main frame. This flosser uses dental floss and delivers fresh floss, while at the same time removing used floss into two separate spools contained within the handle of the flosser. This flosser does not provide for delivery of an inter-dental brush. It does not have means for a cartridge having a plurality of chambers housing at least one inter-dental brush therein that is rotated to present a selected inter-dental brush for use.

U.S. Pat. Nos. 5,495,863 and 7,011,099 to Bergman disclose a flossing device with advancing and tensioning mechanisms. U.S. Published Patent Application No. 2005/0000539 to Bergman discloses a hand held flossing device. The floss is delivered using a one-way ratchet gear from a dental floss spool contained in the handle. After delivery, the used floss is returned back to a shaft that carries the advancing gear, where the used floss is stored. A separate mechanism adjusts the tension of the taut dental floss. This flossing device does not provide for delivery of an inter-dental brush. It contains no means for a cartridge having a plurality of chambers housing at least one inter-dental brush therein that is rotated to present a selected inter-dental brush for use.

U.S. Pat. No. 5,642,741 to Choi discloses a toothpick. A spiral wound wire toothpick is coated with a resin. It is attached to a main body for easy grasping of the toothpick. The '741 patent does not disclose delivery of an inter-dental brush by way of a cartridge having a plurality of chambers housing inter-dental brushes.

U.S. Pat. No. 5,657,780 to Giacopuzzi discloses a dental floss holder having a wedge actuated brake assembly. The handle of the dental floss holder has a supply real that delivers the dental floss to the holding sections, while used dental floss is returned to a take up reel. A brake assembly adjusts the tension of the dental floss. No disclosure is contained by the '780 patent concerning delivery an inter-dental brush.

U.S. Pat. No. 5,718,667 to Sugimoto et al. discloses an oral hygiene instrument. An oral hygiene tool is removably attached to a holder member with a vibration generating means that vibrates the instrument by way of the holder member. This oral hygiene instrument uses an inter-dental cleaning brush or instruments such as tooth brush, a nipple-type gum massaging tool, a gum massaging tool or a floss unit attached to one end of the instrument through a plurality of slits. The instrument has a central cavity that houses a battery and a vibrating generating means. The cavity is closed by a screwed-on end cap with a watertight seal. An inter-dental cleaning brush or other oral hygiene instruments are vibrated. They have to be attached one at a time using the plurality of slots provided. No disclosure is contained within the '667 patent concerning a dedicated instrument for an inter-dental cleaning brush. The hygiene instrument does not provide new brush elements that may be advanced from chambers integrated within a rotating cartridge.

U.S. Pat. No. 5,722,440 to Urso discloses a bite device for driving floss through tight inter-dental gaps. A flossing aid drives a spanned dental floss between the fork of a flossing device. A leaf spring loaded bitable button drives the floss between teeth with small inter-dental space. When the bite is released, the leaf spring pushes the biting element away, permitting flossing operation. No disclosure is contained with the '440 patent concerning an inter-dental brush.

U.S. Pat. No. 5,868,149 to Yang discloses a retractable toothpick. An expanding bi-toothpick has dual controls for pushing and extracting. The retractable toothpick is a slender flexible rod inserted into a curved tube attached to a spring-like V shaped element. Moving the V shaped element pushes the inner toothpick rod in and out between the interstices of the teeth, removing occluded food particles. This retractable toothpick is structurally and functionally distinct from an inter-dental brush that may be refreshed from a continuous brush feed stock advanced from chambers integrated within a rotating cartridge.

U.S. Pat. No. 6,079,424 to Lillbacka discloses a method and arrangement for tensioning dental floss, and a device for cleaning teeth. This device and method is operative to hold and tension dental floss. A tensioning element rotates within the device body; a tensioning passage and a guide passage are located at opposite ends of the tensioning element. The tensioning passage and the guide passage are offset by an angle, which allows the floss to be secured when the tensioning element is rotated, without introducing excessive tension in the strand. This device uses a dental floss which may be withdrawn from a spool and tightened. There is no disclosure in the '424 patent concerning an inter-dental brush that may be renewed from a continuous inter-dental brush feedstock advanced from chambers integrated within a rotating cartridge.

U.S. Pat. No. 6,363,949 to Brown discloses a dental care device. This dental care device combines a flossing tool for dispensing dental floss and holding a length of the floss under tension with a double-edged tongue scraper. The dental care device includes an ergonomic handle. The handle includes a tool storage compartment, which may be used to contain dental hygiene tools such as a microbrush and a pick. The tongue scraper is attached to the end of the handle opposite the floss fork and includes a semicircular blade having opposing edges which are formed so that one of the edges is sharper than the other. This dental care device includes a flossing element on one side and a tongue scraper on the other side. Such a device does not operate to suggest an inter-dental brush. The microbrush provided in the tool storage section of the device does not provide the functionality of an inter-dental brush. No disclosure is contained by the '949 patent concerning a replaceable inter-dental brush that is fed out from an inter-dental brush feed stock of a plurality of inter-dental brushes advanced from chambers integrated within a rotating cartridge.

U.S. Published Patent Application No. 2005/0144747 to Juan discloses an inter-dental brush structure. This inter-dental brush structure comprises a brush shaft installation opening installed on the curved end of the brush handle. A fitting bulge and a joined clip lid are installed on the top surface of the curved end. The joined clip lid has a fitting fillster installed, matching the fitting bulge. The fitting fillister of the joined clip lid can fit the fitting bulge and fix the brush shaft inserted in the brush shaft installation opening by pushing back the rear of the brush shaft and clipping it tight to fix, and in turn enable, the installation and replacement of the brush shaft. The brush handle in formed of two parts connected by an axis so that it can revolve. The connecting surface has several indents and bulges arranged in a circle to fix the location of the revolving handle. The characteristic of this inter-dental brush structure comprises an adjustment to the angle, which is needed for brushing the rear teeth crevices, thereby increasing the convenience of usage. This inter-dental brush accepts new brush elements, which are held in place by a joining clip connected to the rim of the curved surface of the handle. The handle can be rotated to various orientations for inter-dental brushing of hard to reach teeth. The inter-dental brushes are separate elements that are crimped by the joining clip. This structure does not replace inter-dental brushes from a stock of inter-dental brushes advanced from chambers integrated within a rotating cartridge.

U.S. Published Patent Application No. 2005/0247328 to Shen et al. discloses a dental floss holder. This dental floss holder has a spool of dental floss contained within the handle body, so that the dental floss head can be moved up and down. This dental floss holder does not dispense an inter-dental brush.

U.S. Published Patent Application No. 2006/0011211 to Landry discloses a dental floss dispensing and tensioning device. A hand-held dental floss holder, dispenser, floss tensioning, and floss advancing device are disclosed. The handle of the device carries a dental floss spool. Dental floss passes through the fork of the dental flosser and is collected in a collection spool. The floss tension is adjusted by a clutch gear. This '211 device does not does not disclose or suggest use of an inter-dental brush.

U.S. Published Patent Application No. 2006/0011212 to Achepohl et al. discloses a manual advance dental floss holder. This holder has a spool of dental floss, which is fed to the flossing head. Used floss is collected in a spool within the handle. The dental floss is manually advanced and its tension is manually adjusted. The '212 patent does not use an inter-dental brush.

Foreign Patent Application No. JP 08-056749 to Kageyama et al. discloses a sanitary article holding device. A holding device is provided wherein a sanitary article can be replaced cleanly, and which provides favorable usage operation. The sanitary article is a toothbrush; not an inter-dental brush. The brush is ejected from a holder, but the device does not provide a cartridge having a plurality of chambers housing at least one inter-dental brush therein that is rotated to present a selected inter-dental brush for use.

Foreign Patent Application No. JP 2004-313446 to Ikemoto discloses an inter-dental cleaning implement. A brush is attached to a metallic rod and slides through a storage device. The storage device has a slot through which a projecting end of the metallic rod can slide to move the inter-dental brush through an opening in the teeth. The brush is not said to be removable from the metallic rod. It is not delivered from a cartridge having a plurality of chambers housing at least one inter-dental brush therein that is rotated to present a selected inter-dental brush for use.

Notwithstanding the efforts of prior art workers to construct a dental hygiene device, and particularly an inter-dental cleaning brush assembly, there exists a need in the art for facile removal of a worn inter-dental brush and rapid replacement thereof with a fresh inter-dental brush. Ready replacement of worn inter-dental brushes would encourage use of the device, thereby promoting improved oral hygiene even in cases where inter-tooth gaps exist. Particularly, there is a need in the art for an inter-dental brush assembly that achieves a virtually continuous feed of inter-dental brush by providing a cartridge having a plurality of chambers each housing at least one inter-dental brush therein that rotates to align a respective chamber to select the desired inter-dental brush which is fed out of an oral portion for use, enabling excision of the used inter-dental brush and the selection and production of a fresh inter-dental brush upon demand.

SUMMARY OF THE INVENTION

The present invention provides an inter-dental brush that is especially suited for use in cases where inter-tooth gaps exist. The inter-dental brush is easy to use and readily refreshed when worn by new inter-dental brush advanced from stock housed within a plurality of chambers constructed within a rotating cartridge. Removal of a worn inter-dental brush and replacement thereof with a fresh inter-dental brush is effected in an efficient, economical manner. Manually challenging maneuvers previously required when sticking metallic wires and rods carrying discrete brush segments into slots within the device handle are virtually eliminated. Ready replacement of worn inter-dental brushes encourages use of the inter-dental brush device, and improved oral hygiene is promoted.

Generally stated, the inter-dental device comprises a handle that accepts a cartridge having a plurality of chambers each appointed for housing at least one replaceable inter-dental brush therein. Each of the chambers comprises an elongated groove extending between a first opening and a second opening and each groove of each chamber is adapted to house at least one inter-dental brush therein. The cartridge is appointed to be rotated to align and select one of the chambers for feed out of a selected inter-dental brush that is housed in the particular chamber. The handle includes an elongated portion, a proximal end and a distal end. An internal plate with an inter-dental brush aperture is constructed near/in association with the proximal end of the handle. Further, the proximal end is appointed to receive an oral portion, while the distal end of the handle is appointed to receive a base portion. The base portion removably attaches to the distal end of the handle portion and includes rotation engagement means adapted to interact with the cartridge removably housed within the elongated portion to engage rotation of the cartridge in alignment and selection of the chamber and visa vie the inter-dental brush housed therein selected for use. The oral portion has an aperture for feeding out the selected inter-dental brush. Upon being used and worn out the selected inter-dental brush is adapted to be discarded and fresh inter-dental brush is adapted to be presented for use. A delivery means in association with the handle and the oral portion is provided and is adapted to feed out the selected inter-dental brush from the respective chamber of the cartridge. Used and worn out inter-dental brush is discarded prior to feeding out fresh inter-dental brush.

Prior to feeding out fresh inter-dental brush from the chambers, substantially all of the used, worn out inter-dental brush must be snipped off or the brush discarded to be replaced with a fresh, clean brush. This is accomplished by a number of ways, including discarding the whole inter-dental brush (and replacing a new brush in the chamber for later use), using an optional slidable cutter to cut the used portion of the brush, or to utilize a fresh new small inter-dental brush fed from an abutting linear arrangement or piggyback formation within a chamber of the cartridge.

BRIEF DESCRIPTION OF THE DRAWING

The invention will be more fully understood and further advantages will become apparent when reference is had to the following detailed description of the preferred embodiments of the invention and the accompanying drawings, in which.

DETAILED DESCRIPTION OF THE INVENTION

Figure 1A:
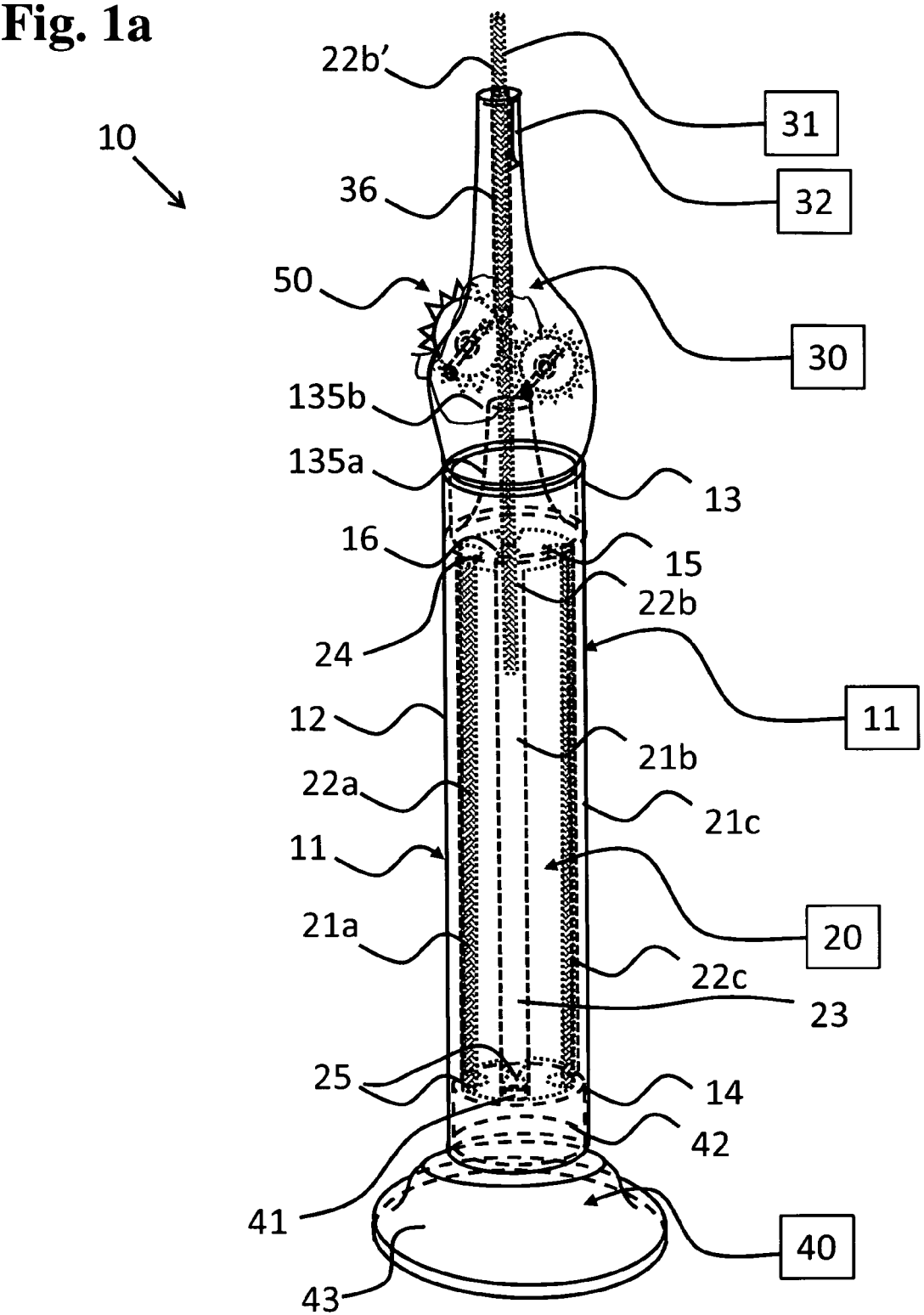
FIG. 1a depicts a schematic view of an embodiment of the inter-dental brush device showing feedstock of a selected inter-dental brush being delivered from a chamber of the cartridge to the oral portion's aperture by a first gear drive.

This invention relates to a continuous feed inter-dental brush and device that provides fresh segments of inter-dental brush from a plurality of chambers located within a cartridge contained within the handle of the device. A continuous feed is effectuated, and the fresh segments are delivered, by turning a knob that drives a selected inter-dental brush from a selected chamber interstitially located in a cartridge located in the handle portion of the device. The user simply aligns the chamber containing the selected inter-dental brush with an inter-dental brush aperture located in a proximal end of the handle and delivers the selected inter-dental brush through the inter-dental brush aperture into the oral portion. The delivery means then grasps the inter-dental brush and guides the inter-dental brush through an aperture of the oral portion and extends same for use. The amount of inter-dental brush extended from the aperture of the oral portion is controlled by the user based on the number of rotations achieved in operating the delivery means. After use, the used and worn out brush portion is either removed from the device or cut by the user using an optional slidable knife before turning the brush delivery knob.

Generally stated, the invention comprises a virtually continuous feed inter-dental brush and device that utilizes a plurality of inter-dental brushes housed within chambers of a removable cartridge placed within the handle of the brush. The inter-dental device is particularly suited for use by those persons concerned with the treatment and/or prevention of gum disease. The inter-dental device is equipped with a rotating internal brush cartridge including a plurality of chamber therein for housing inter-dental brushes that effectuates a continuous feed of brush to the user. In this manner, there is provided a more sanitary, more effective, longer lasting, and more economical apparatus. Use of the inter-dental device facilitates maintenance of proper oral hygiene. It promotes the health and beauty of the mouth, gums, and teeth.

There are many products and devices on the market, which help people maintain hygiene within the oral cavity. Such products include toothbrushes, floss, mouth rinse, toothpaste, and the like. One such device used to maintain proper oral health is the inter-dental brush device. An inter-dental brush device includes a handle and a brush attached to the end of the handle. The size and shape of the brush is designed to allow a user to insert the brush in-between the teeth to cleanse and massage, and remove tartar and food from the space along the gum line and in-between the teeth. Proper oral hygiene includes daily flossing or use of an inter-dental brush device. Many people prefer to use an inter-dental brush instead of floss because of its ease of use especially when the gap between the teeth is large. Over time, the brush portion of the inter-dental brush device wears out and the brush material becomes ineffective or defective in its teeth cleaning ability. At this point the entire inter-dental brush device, including the handle, must be discarded and replaced with a brand new inter-dental brush device.

Prior art inter-dental brush devices have a one size only brush head. Users must frequently discard the entire inter-dental brush device and replace it with a brand new one. Oftentimes, the user does not have a replacement inter-dental brush device on hand. Further, the process of continuously replacing the inter-dental brush device becomes rather costly. Accordingly, there remains a need in the art for an improved inter-dental brush device having an internal, replaceable brush cartridge that provides a continuous feed inter-dental brushes through a plurality of chambers. Further, there is a need in the art for an inter-dental brush device that provides the ability to store and feed inter-dental brushes of different or varying diameters so that a user can choose the inter-dental brush he/she needs based on the tooth gap size being cleaned, selecting a larger diameter brush for larger gaps and a smaller diameter brush for smaller gaps.

A brush cutter may be provided in the oral portion, which slides out to cut the used, worn out inter-dental brush prior to operating the gear to advance a fresh inter-dental brush from the cartridge. The cutter cuts the wire portion of the inter-dental brush which carries the brush elements. The cutter is disposed on the underside face of the slidable cutter, which slides on two parallel grooves on the angular portion of the handle. When the cutting operation is complete, the cutter slides back into the oral portion.

Figure 1B:
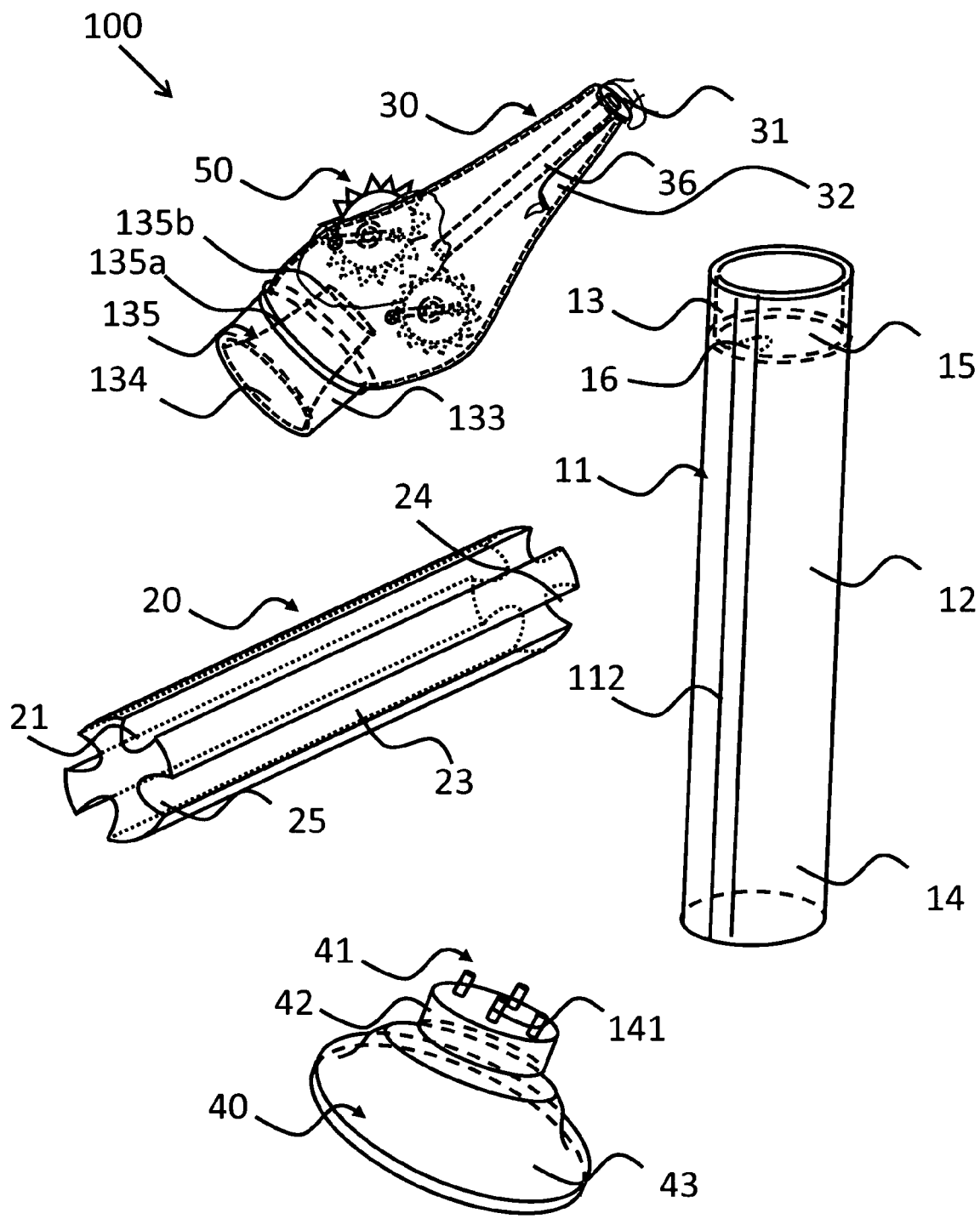
FIG. 1b depicts the inter-dental brush device dismantled, showing the handle, oral portion, cartridge and base portion.

FIG. 1a depicts generally at 10 a schematic view of an embodiment of the inter-dental brush device showing feedstock of a selected inter-dental brush being delivered from a chamber of the cartridge to the oral portion's aperture by a first gear drive. FIG. 1b depicts the inter-dental brush device dismantled, showing the handle (preferably being composed of a transparent polymeric material), oral portion, cartridge and base portion, shown generally at 100. Regarding FIGS. 1a and 1b, the inter-dental device 10 comprises a handle 11 that accepts a cartridge 20 having a plurality of chambers 21 (21a, 21b, 21c-21n) each appointed for housing at least one replaceable inter-dental brush 22 (22a, 22b, 22c-22n) therein. Each of the chambers 21 (21a-21n) comprises an elongated groove 23 extending between a first opening 24 and a second opening 25 and each groove 23 of each chamber 21 is adapted to house at least one inter-dental brush 22 therein. Second opening 25 is appointed to provide the ability to replace inter-dental brushes 22 in each respective emptied or substantially emptied chamber 21. Substantially emptied chamber 21 may result in a situation where a respective inter-dental brush 22 is mostly utilized and only a small portion remains as same has been used and used portions cut from the remainder of the inter-dental brush 22. As shown, cartridge 20 is appointed to be rotated to align and select one of the chambers 21b (herein selected) for feed out of the respective selected inter-dental brush 22b, that is housed in chamber 21b. Cartridge 20 preferably includes between two to ten chambers 21 (21a-21j). Most preferably, as shown in FIGS. 1a and 1b, cartridge 20 has four chambers 21 (21a-21d). Each of the chambers 21 (21a-21n) have a chamber diameter. Preferably, at least one of the chamber diameters is different for housing inter-dental brushes 22 having varying diameters so that some of the inter-dental brushes 22 have a larger diameter for cleaning larger gaps in the teeth. As shown in FIG. 1a, at least one of said inter-dental brush is constructed as an elongated continuous feed inter-dental brush 22b, 22c that is appointed to be singly housed within one of the brush chambers 21b, 21c and brush 22b, 22c is continuously fed out from brush chamber 21b, 21c and discarded upon use or the used portion cut via optionally cutter 33 in oral portion 30 (shown also in FIG. 2a). Optionally, the inter-dental brush is provided as a plurality of small inter-dental brushes arranged in abutting linear formation, as is shown in FIG. 2b.

Inter-dental brush 10 generally includes handle 11, an oral portion 30, a base portion 40, cartridge 20 and delivery means 50. Handle 11 includes an elongated portion 12, a proximal end 13 and a distal end 14. An internal plate 15 with an inter-dental brush aperture 16 is constructed near/in association with proximal end 13 of handle 11. Further, proximal end 13 is appointed to receive oral portion 30, while distal end 14 of handle 11 is appointed to receive a base portion 40. Oral portion 30 includes a bottom 133 (shown in FIG. 1b) that is generally received within proximal end 13 of handle 11. This may be achieved by providing a snapping fit engagement or by providing a screw on engagement. Oral portion 30 is shown having a relatively straight end wherein aperture 31 sits; the oral portion 30 may be provided so that end is more curved, or angled or provide with a taper and slightly curved. Bottom 133 of oral portion 30 may be constructed with a large bottom aperture 134 and further provided with a guidance funnel 135 having funneling walls 135a and a funnel aperture 135b that are in alignment with delivery means 50, which in turn is in alignment with an aperture 31 of oral portion 30.

Base portion 40 removably attaches to distal end 14 of handle 11 and includes rotation engagement means 41 adapted to interact with cartridge 20 removably housed within elongated portion 12 to engage rotation of cartridge 20 in alignment and selection of chamber 21b (21a-21n) and visa vie the inter-dental brush 22b (22a-22n) housed therein selected for use. Base portion 40 generally comprises a platform 43 and an insertion portion 42 that is received within distal end 14 of handle 11, preferably via snap fit, and is in a rotational arrangement so that base portion 40 is able to be rotated. In turn, rotation of base portion 40 engages rotation of cartridge 20 for alignment of chambers 21 in the selection of inter-dental brushes 22. Rotation engagement means 17 of base portion 40 may comprise a ridge or nodule that is appointed to matingly engage with cartridge 20 to induce rotation of cartridge 20 within handle 11. Rotation engagement means 17 may be provided as a slight nodule in the center of insertion portion 43 for causing pressure on cartridge 20 and thereby causing same to rotate. In another embodiment, and as shown, rotation engagement means 41 of base portion 40 comprises a plurality of nodules 141 (shown in FIG. 1b) that are each appointed to be received within second opening 25 of each of brush chambers 21 to matingly engage cartridge 20 and induce rotation within handle 11 as base portion 40 is rotated.

Preferably, cartridge 20 and handle 11 are cylindrical in shape. Further, preferably handle 11 includes an alignment marker thereon for facilitating alignment of the selected chamber 21b housing the selected inter-dental brush 22b with inter-dental brush aperture 16 of proximal end 13 of handle 11, for further alignment with delivery means 50 and aperture 31 of oral portion 30 for feed out of selected inter-dental brush 22b. Preferably this alignment marker is located as a colored line located on elongated portion 12 as shown in FIG. 2 at 112, or other form of indicator.

Oral portion 30 has an aperture 31 for feeding out selected inter-dental brush 22b, with the extended portion shown at 22b'. Preferably, oral portion 30 includes an internal aperture guide 36 that is a tube-like member wherein inter-dental brush 21b is directed by delivery means 50. Upon being used, the used and worn out segment 22b' of the selected inter-dental brush 22b is adapted to be discarded and fresh inter-dental brush 22b is adapted to be presented for use. This is preferably achieved by way of a cutting device 32 located in oral portion 30 (shown in detail in FIG. 4 and discussed herein as per the FIG. 4 discussion). A delivery means 50 in association with handle 11 and oral portion 30 is provided and is adapted to feed out the selected inter-dental brush 22b from the respective chamber (21b) of cartridge 20. Used and worn out inter-dental brush segments 22b' is discarded prior to feeding out fresh inter-dental brush.

In operation, generally, a brush is selected via alignment of the chamber with the inter-dental aperture of the proximal end of the handle, and the device is inverted and shaken so that the selected inter-dental brush enters the oral portion and the delivery means is rotated to catch the brush and drive the brush up out of the aperture of the oral portion for use. Brushes 22a-22n preferably have a length ranging between three to five inches—corresponding to the length of the elongated portion of the handle. Channels/chambers 21a-21n may be of the same diameter, but still be adapted to receive brushes 22a-22n of different diameters. The cartridge is generally in the form of a cylinder and preferably includes 4 or 5 grooved cylinder chambers 21 that hold brushes therein. Each chamber 21 is formed as a channel and is appointed to hold one or more inter-dental brushes 22 and the different channels could conceivably hold brushes of different diameters. The cartridge rotates to a designated spot which allows the user to bring one of the chambers housing a brush to a single opening (inter-dental aperture 16) which would allow that brush to drop into contact with the delivery means 50 (preferably provided as gears/rollers) which bring the brush forward and out of the device for use. The gears/rollers are provided as two wheels with teeth or gears that grab the brush and bring it forward when a wheel outside the device is turned—or when one of the wheels having a portion showing outside of the device is turned. This wheel would allow the user to roll out whatever length of brush they desired and optionally retract the brush back into the device when not in use. When the brush is worn out another brush could follow from the same chamber, or from another chamber by again rotating the cartridge to reveal a different chamber with new brushes. The platform portion of the base portion is a flat surface located at the end of the device so that it can stand up when not in use. This base portion is removable, revealing the chambers in the rotating cartridge so that replacement brushes can be inserted when they are all worn out or exhausted/depleted.

Figure 2A:
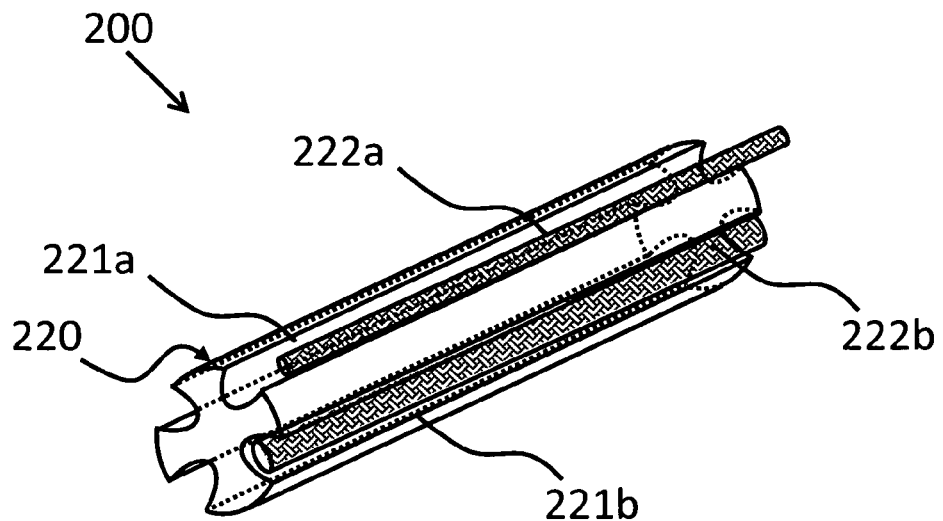
FIG. 2a illustrates a view of the cartridge with elongated inter-dental brushes having varying diameters is housed within chambers.
Figure 2B:
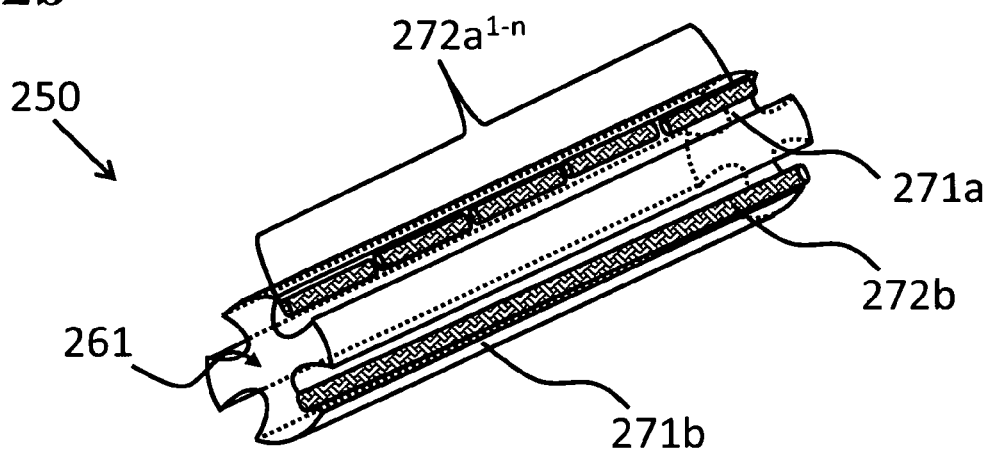
FIG. 2b illustrates a view of the cartridge with an elongated inter-dental brush located in a chamber and a plurality of small inter-dental brushes arranged in an abutting linear formation in another chamber.

FIGS. 2a and 2b illustrate views of the cartridge with inter-dental brushes therein, shown at 200 and 250 respectively. Particularly, FIG. 2a illustrates a cartridge 211 having varying diameter inter-dental brushes housed therein, shown at 222a and 222b in chambers 221a and 221b, respectively. Herein, inter-dental brush 222a has a smaller diameter than inter-dental brush 222b. FIG. 2b illustrates a cartridge 261 with an elongated inter-dental brush 272b located in a chamber 271b, and a plurality of small inter-dental brushes $272a^{1-n}$ arranged in an abutting linear formation in another chamber 271a. In this arrangement as a small inter-dental brush 272a is used, the brush is discarded and a new small inter-dental brush is appointed to be presented for use.

Figure 3A:
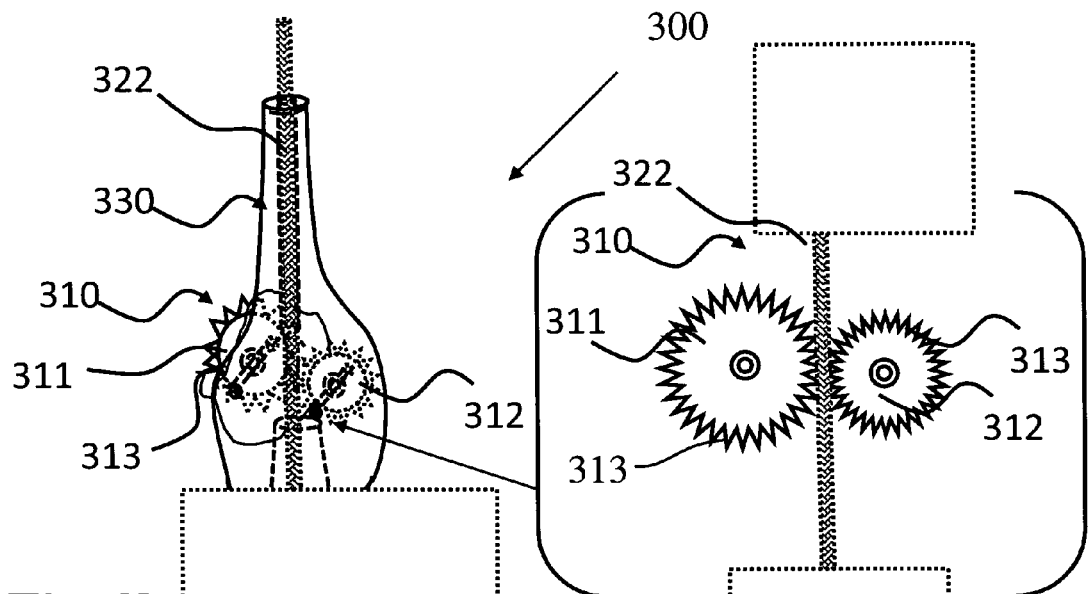
FIG. 3a illustrates a sectional view of an embodiment of the delivery means wherein a first and second gear act in concert to deliver the selected inter-dental brush through the aperture in the oral portion to present a portion of the inter-dental brush for use.
Figure 3B:
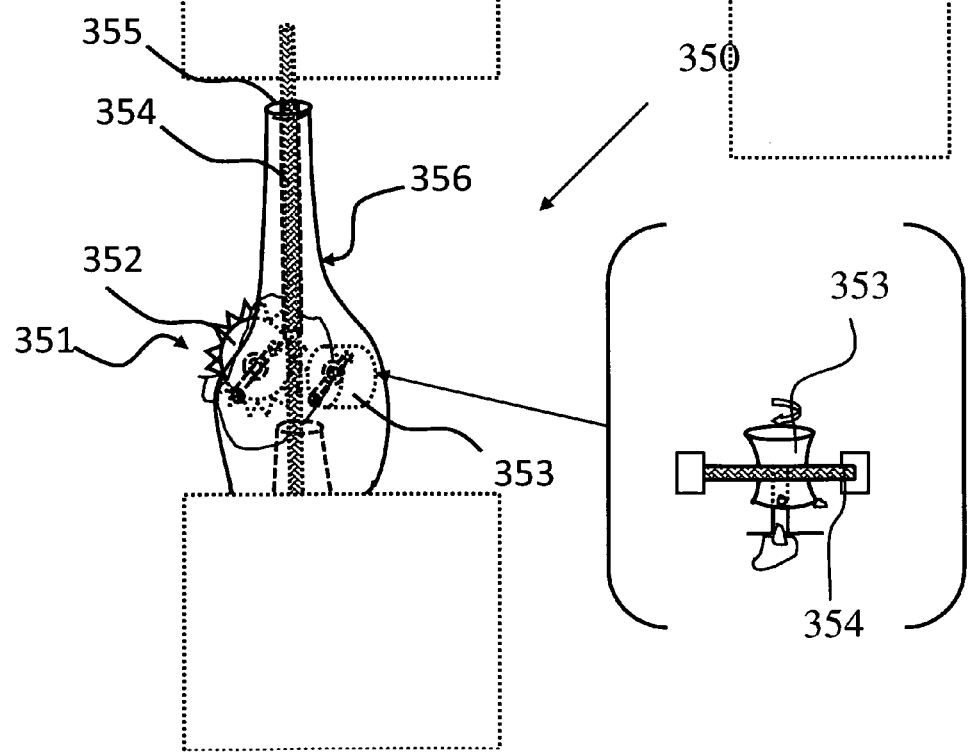
FIG. 3b illustrates a sectional view of another embodiment of the delivery means wherein a first gear acts in concert with a rotating wheel to deliver the selected inter-dental brush through the aperture in the oral portion to present a portion of the inter-dental brush for use.

FIGS. 3a and 3b illustrate sectional views of the delivery means, shown generally at 300 and 350. Particularly, in FIG. 3a a delivery means 310 is provided wherein a first and second gear, 311 and 312 are provide. First gear 311 and second gear 312 act in concert to deliver the selected inter-dental brush through the aperture in the oral portion 330 to present a portion of the inter-dental brush for use. First gear 311 is constructed so that it protrudes from oral portion 330 while the rest of gear 311 is located within oral portion 330 so that the first gear 311, which includes teeth 313 that grasp the inter-dental brush 322 and causes same to move forward and a portion to become ejected from oral portion 330 for use. Second gear 312 also rotates as gear 311 rotates and brush 322 runs along second gear 312. Second gear 312 preferably includes teeth 313 thereon for engaging and pulling brush 322.

FIG. 3b illustrates a sectional view of another embodiment of a delivery means 351 wherein a first gear 352 acts in concert with a rotating wheel/swivel 353 to deliver the selected inter-dental brush 354 through the aperture 355 in the oral portion 356 to present a portion of the inter-dental brush for use. The gear 352 comprises a plurality of teeth adapted to grab onto the brush material as it passes out of the chamber of the cartridge into the oral portion's aperture for use. The swivel 353 rotates as brush material is fed out. The continuous feed of brush 354 material is spooled against the swivel 353 and same is guided forward.

Figure 4:
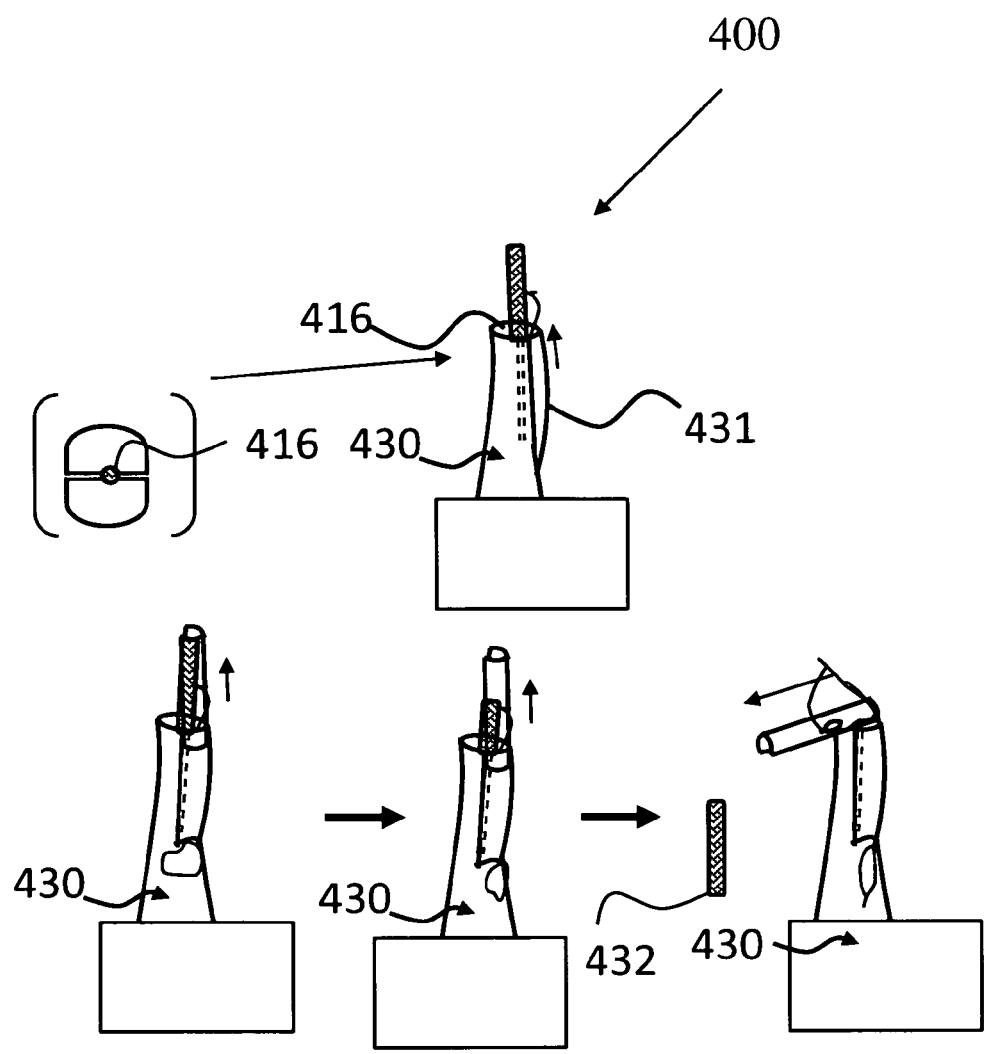
FIG. 4 depicts an optional slidable cutter on the oral portion adapted to cut off the used, worn out inter-dental brush prior to feeding out fresh inter-dental brush from the feedstock contained within the chambers of the cartridge.

FIG. 4 depicts an optional slidable cutter on the oral portion adapted to cut off the used, worn out inter-dental brush prior to feeding out fresh inter-dental brush from the feedstock contained within the chambers of the cartridge, shown generally at 400. Oral portion 430 includes the optional slidable cutter 431 which is a movable to operable cut off the unwanted portion of used brush material exiting the aperture 416 or oral portion 430 prior to feeding out new brush material from the device. The moving slide portion further comprises a cutter blade on its underside, which cuts off the used, worn out inter-dental brush 432, as shown. The moving slide portion moves along a channel section of the oral portion 430. The slidable cutter 431 is moved back into the oral portion 430 after cutting the worn out inter-dental brush.

Preferably the delivery means are provided with a locking means to prevent the selected inter-dental brush from traveling back into the oral portion and the brush chamber from where it feeds. This can be accomplished by providing locking of the gears and prevention of reverse motion thereof via a click stop in the wheel mechanism of the delivery means. In another embodiment, the oral portion includes a locking means to prevent the selected inter-dental brush from traveling back into the oral portion and the chamber from where it feeds, such as providing that the aperture of the oral portion includes a spring loaded closure that tightly grasps the inter-dental brush extending therefrom (i.e. such as with some mechanical pencils).

By providing an inter-dental brush device with a feed of inter-dental brushes, the inter-dental device of the present invention enjoys a long service life with the ability to replace used and worn out inter-dental brushes with a fresh supply. The diameter of the inter-dental brushes can vary depending on the size of the tooth gaps to be serviced. Generally, the inter-dental brush has a diameter of about 0.25 to 0.125 inch. The inter-dental device makes the care of one's mouth, teeth, and gums much easier. The user is able to select the appropriate length of brush material to suit his particular tooth architecture. At the same time, the inter-dental device is very economical, because it uses replaceable inter-dental brushes housed within chambers of the cartridge. The inter-dental device is suitable for both travel and home use.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. An inter-dental brush device, comprising:
   a. a handle that accepts a cartridge having a plurality of chambers each appointed for housing at least one replaceable inter-dental brush therein, each of said chambers comprising an elongated groove extending between a first opening and a second opening and being adapted to house said inter-dental brush therein, said cartridge being appointed to be rotated to align and select one of said chambers for feed out of a selected inter-dental brush;
   b. said handle having an elongated portion, a proximal end and a distal end, said proximal end having an internal plate with an inter-dental brush aperture and said proximal end being appointed to receive an oral portion, said distal end of said handle being appointed to receive a base portion;
   c. said base portion having rotation engagement means adapted to interact with said cartridge to rotatably move said base portion to align said aperture with said chamber and enable selection of said inter-dental brush;
   d. said oral portion having an aperture for feeding out said selected inter-dental brush for use, upon being used and worn out said selected inter-dental brush is adapted to be discarded and fresh inter-dental brush is adapted to be presented for use; and
   e. a delivery means in association with said handle and said oral portion adapted to feed out said selected inter-dental brush;
   whereby said used and worn out said selected inter-dental brush is discarded prior to feeding out fresh inter-dental brush by said delivery means.

2. An inter-dental brush device as recited by claim 1, wherein said cartridge has at least four of said chambers.

3. An inter-dental brush device as recited by claim 1, wherein each of said chambers have a chamber diameter, wherein at least one of said chamber diameter is different, and wherein said inter-dental brushes each have a brush diameter corresponding to each of said chambers to provide delivery and use of said inter-dental brushes having at least one different diameter.

4. An inter-dental brush device as recited by claim 1, wherein at least one of said inter-dental brush is constructed as an elongated continuous feed inter-dental brush that is appointed to be singly housed within one of said brush chambers and said brush is continuously fed out from said brush chamber and discarded upon use.

5. An inter-dental brush device as recited by claim 4, wherein said oral portion includes a cutting means appointed to cut off said used and worn out inter-dental brush prior to feeding out fresh inter-dental brush.

6. An inter-dental brush device as recited by claim 5, wherein said cutting means includes a slidable cutter having a pair of grooves in said oral portion.

7. An inter-dental brush device as recited by claim 6, wherein said slidable cutter has a cutting blade on an underside thereof.

8. An inter-dental brush device as recited by claim 1, wherein a plurality of small inter-dental brushes arranged in abutting linear formation are housed within at least one of said chambers of said cartridge providing a continuous feed of said small inter-dental brushes that are continuously fed out from said brush chamber and discarded upon use to be replaced with fresh abutting said small inter-dental brush from said linear formation.

9. An inter-dental brush device as recited by claim 1, wherein said rotation engagement means of said base portion comprises a ridge or nodule that is appointed to matingly engage with said cartridge to induce rotation of said cartridge within said handle.

10. An inter-dental brush device as recited by claim 9, wherein said rotation engagement means of said base portion comprises a plurality of nodules that are each appointed to be received within said second opening of each of said brush chambers to matingly engage said cartridge and induce rotation within said handle as said base portion is rotated.

11. An inter-dental brush device as recited by claim 1, wherein said cartridge and said elongated handle are cylindrical in shape.

12. An inter-dental brush device as recited by claim 1, wherein said elongated portion of said handle includes an alignment marker thereon for facilitating alignment of said chamber housing said selected inter-dental brush with said inter-dental brush aperture of said proximal end of said handle, for further alignment with said delivery means and said aperture of said oral portion for feed out of said selected inter-dental brush.

13. An inter-dental brush device as recited by claim 1, wherein said oral portion includes a guidance funnel in alignment with said delivery means.

14. An inter-dental brush device as recited by claim 1, wherein said delivery means are provided with a locking means to prevent said selected inter-dental brush from traveling back into said oral portion and said brush chamber from where it feeds.

15. An inter-dental brush device as recited by claim 1, wherein said oral portion includes a locking means to prevent said selected inter-dental brush from traveling back into said oral portion and said chamber from where it feeds.

16. An inter-dental brush device as recited by claim 1, wherein said delivery means includes a first gear for feeding out said continuous inter-dental feedstock.

17. An inter-dental brush device as recited by claim 16, wherein said delivery means further includes a second gear acting in conjunction with said first gear for feeding out said continuous inter-dental feedstock.

18. An inter-dental brush device as recited by claim 16, wherein said delivery means further includes a wheel acting in conjunction with said first gear for feeding out said continuous inter-dental feedstock.

* * * * *